(12) United States Patent
Ward

(10) Patent No.: US 7,321,118 B2
(45) Date of Patent: Jan. 22, 2008

(54) SCANNING TRANSMISSION ION MICROSCOPE

(75) Inventor: Billy W. Ward, Merrimac, MA (US)

(73) Assignee: ALIS Corporation, Peabody, MA (US)

( * ) Notice: Subject to any disclaimer, the term of this patent is extended or adjusted under 35 U.S.C. 154(b) by 0 days.

(21) Appl. No.: 11/147,102

(22) Filed: Jun. 7, 2005

(65) Prior Publication Data

US 2006/0284092 A1 Dec. 21, 2006

(51) Int. Cl.
*H01J 37/30* (2006.01)

(52) U.S. Cl. .................. 250/309; 250/310; 250/306

(58) Field of Classification Search ................. 250/309
See application file for complete search history.

(56) References Cited

U.S. PATENT DOCUMENTS

| | | | |
|---|---|---|---|
| 3,602,710 A * | 8/1971 | Mueller | 250/309 |
| 3,868,507 A * | 2/1975 | Panitz | 250/287 |
| 4,044,255 A | 8/1977 | Krisch et al. | |
| 4,139,773 A * | 2/1979 | Swanson | 250/423 R |
| 4,236,073 A * | 11/1980 | Martin | 250/306 |
| 4,352,985 A * | 10/1982 | Martin | 250/306 |
| 4,451,737 A | 5/1984 | Isakozawa | |
| 4,467,240 A | 8/1984 | Futamoto et al. | |
| 4,639,301 A | 1/1987 | Doherty et al. | |
| 4,721,878 A | 1/1988 | Hagiwara et al. | |
| 4,874,947 A * | 10/1989 | Ward et al. | 250/309 |
| 4,954,711 A | 9/1990 | Fink et al. | |
| 5,034,612 A | 7/1991 | Ward et al. | |
| 5,188,705 A | 2/1993 | Swanson et al. | |
| 5,414,261 A | 5/1995 | Ellisman et al. | |
| 5,750,990 A | 5/1998 | Mizuno et al. | |
| 5,783,830 A | 7/1998 | Hirose et al. | |
| 5,976,390 A | 11/1999 | Muramatsu | |
| 6,042,738 A | 3/2000 | Casey et al. | |
| 6,211,527 B1 | 4/2001 | Chandler | |
| 6,268,608 B1 | 7/2001 | Chandler | |
| 6,354,438 B1 | 3/2002 | Lee et al. | |
| 6,395,347 B1 | 5/2002 | Adachi et al. | |
| 6,414,307 B1 | 7/2002 | Gerlach et al. | |
| 6,504,151 B1 | 1/2003 | Mitchell et al. | |
| 6,538,254 B1 | 3/2003 | Tomimatsu et al. | |
| 6,579,665 B2 | 6/2003 | Lee et al. | |
| 6,700,122 B2 | 3/2004 | Matsui et al. | |

(Continued)

FOREIGN PATENT DOCUMENTS

EP 0 477 992 A2 4/1992

(Continued)

OTHER PUBLICATIONS

Fink, H.-W., "Mono-atomic tips for scanning tunneling microscopy", IBM J. Res. Develop. 30: 460-465 (1986).

(Continued)

*Primary Examiner*—David Vanore
(74) *Attorney, Agent, or Firm*—Fish & Richardson P.C.

(57) ABSTRACT

Scanning Transmission Ion Microscope. The microscope includes a bright helium ion source to generate an ion beam and a focusing electrostatic optical column to focus the ion beam. A translation stage supports a sample to receive the focused ion beam and a detector responds to ions transmitted through the sample to generate a signal from which properties of the sample may be displayed.

20 Claims, 1 Drawing Sheet

U.S. PATENT DOCUMENTS

| | | | |
|---|---|---|---|
| 6,753,535 | B2 | 6/2004 | Rose |
| 6,791,084 | B2 | 9/2004 | Shimoma et al. |
| 6,822,245 | B2 | 11/2004 | Muto et al. |
| 6,875,981 | B2* | 4/2005 | Nishikawa .................. 250/306 |
| 7,084,399 | B2 | 8/2006 | Muto et al. |
| 2002/0134949 | A1 | 9/2002 | Gerlach et al. |
| 2002/0144892 | A1 | 10/2002 | Lee et al. |
| 2003/0062487 | A1 | 4/2003 | Hiroi et al. |
| 2004/0031936 | A1 | 2/2004 | Oi et al. |
| 2004/0121069 | A1 | 6/2004 | Ferranti et al. |
| 2006/0060777 | A1* | 3/2006 | Motoi ........................ 250/309 |
| 2006/0097166 | A1 | 5/2006 | Ishitani et al. |
| 2006/0197017 | A1* | 9/2006 | Motoi et al. ................ 250/310 |
| 2007/0025907 | A1 | 2/2007 | Rezeq et al. |

FOREIGN PATENT DOCUMENTS

| | | |
|---|---|---|
| GB | 1 604 898 | 12/1981 |
| JP | 5209844 | 12/1983 |
| JP | 1-130450 | 5/1989 |
| JP | 07045230 | 2/1995 |
| JP | 2001/176440 | 6/2001 |

OTHER PUBLICATIONS

Fink, H.-W., "Point Source for Ions and Electrons", Physica Scripta 38: 260-263 (1988).
Binh, V.T., "In situ fabrication and regeneration of microtips for scanning tunneling microscopy", J. Microscopy 152(2): 355-361 (1988).
Stocker, W. et al., "Low-energy electron and ion projection microscopy", Ultramicroscopy 31: 379-384 (1989).
Bell, A.E. et al., "High-field ion sources", Rev. Sci. Instrum. 61(1): 363-365 (1990).
Schmid, H. et al., "Combined electron and ion projection microscopy", Appl. Surf. Sci. 67: 436-443 (1993).
Muller, H.U. et al., "Emission properties of electron point sources", Ultramicroscopy 50: 57-64 (1993).
Horch, S. et al., "Field emission from atomic size sources", J. Appl. Phys. 74(6): 3652-3657 (1993).
Fink, H.-W. et al., "Electron and Ion Microscopy Without Lenses", *Nanostructures and Quantum Effects* (Springer-Verlag, 1994), pp. 17-27.
Edinger, K. et al., "Development of a high brightness gas field ion source", J. Vac. Sci. Technol. B 15(6): 2365-2368 (1997).
Horiuchi, K. et al., "Emission characteristics and stability of a helium field ion source", J. Vac. Sci. Technol. B. 6(3): 937-940 (1988).
Melngailis, J., "Focused ion beam technology and applications", J. Vac. Sci. Technol. B 5(2): 469-495 (1987).
Fu, T.-Y. et al., "Method of creating a Pd-covered single-atom sharp W pyramidal tip: Mechanism and energetics of its formation", Phys. Rev. B 64: 113401-1-4 (2001).
Lucier, A.-S., "Preparation and Characterization of Tungsten Tips Suitable for Molecular Electronics Studies", excerpts from MSc Thesis, McGill University, 2004.
Fotino, M., "Tip sharpening by normal and reverse electrochemical etching", Rev. Sci. Instrum. 64(1): 159-167 (1993).
Wengelnik, H. et al., "Oxygen-induced sharpening process of W(111) tips for scanning tunneling microscope use," J. Vac. Sci. Technol. A 8(1): 438-440 (1990).
Rezeq, M. et al., "Sharpening of a Field of Ion Microscope (FIM) Tungsten Tip by the Controlled Interation of Nitrogen with the Tip Surface Atoms," Abstract from APS March Meeting (2004).
McGuinness, P.E., "Seeing at Atomic Resolution is Believing: Welcome the Helium Ion Microscope", Scanning 27(6): 323 (2005).
Notte, J. et al., "Sample Interaction and Contrast Mechanisms of the Helium Ion Microscope" (Scanning Conference, Apr. 2006).
Notte, J.A. et al., "An Introduction to Helium Ion Microscopy and its Nanotechnology Applications" (NanoScience and Technology Institute, May 2006).
Ward, B.W. et al., "The Helium Ion Microscope: A New Tool for Nanoscale Microscopy and Metrology" Electron, Ion, and Photon Beam Nanotechnology Conference, May 2006).
Morgan, J. et al., "An Introduction to the Helium Ion Microscope" (Microscopy Today, Jul. 2006).
Hill, R. et al., "The ALIS He Ion Source and its Application to High Resolution Microscopy" (Seventh International Conference on Charged Particle Optics, Jul. 2006).
Notte, J. et al., "An Introduction to Helium Ion Microscopy" (Microscopy and Micro-Analysis, Jul. 2006).
"An Introduction to the Helium Ion Microscope" (Materials Research Society Meeting, Nov. 2006).
J. Melngailis, "Ion Sources for Nanofabrication & High Resolution Lithography," IEEE Proceedings of the 2001 Particle Accelerator Conference, Chicago, Illinoise, (2002).
K. Jousten et al. "Growth & Current Charities of a Stable field Ion Emitter," Ultramicroscope 26, pp. 301-312 (1988).
Qing Ji, "Maskless, Resistless Ion Beam Lithography Process," Ph.D. Dissertation, Department of Electrical Engineering and Computer Sciences, UCAL Berkeley (2003).
Escovitz et al., "Scanning Transmission Ion Microscope with a Field Ion Source," Feb. 24, 1975, Proceedings of the National Academy of the Sciences, vol. 72, No. 5, Published May 1975, pp. 1826-1828.
Russell P.E. et al., "Chemically and geometrically enhanced focused ion beam micromachining," Journal of Vacuum Science and Technology B, vol. 16, No. 4, Jul./Aug. 1998, 2494-2498.
Schmid et al., "In-line holography using low-energy electrons and photons: Applications for manipulation on a nanometer scale," Journal of Vacuum Science & Technology B: Microelectronics and Nanometer Structures, Nov. 1995, vol. 13, Issue 6, pp. 2428-2431.
Fink et al., "Atomic Resolution in Lensless Low-energy Electron Holography," Phys. Rev. Lett. 67, Issue 12-16 Sep. 1991, pp. 1543-1546.
Brune et al., "Surface migration of "hot" adatoms in the course of dissociative chemisorption of oxygen on AI(111)," Phys. Rev. Lett. 68, Issue 5-3 Feb. 1992, pp. 624-626.
Fink et al., "Lattice Steps and Adatom Binding on Tungsten (211)," Surf. Sci., vol. 143, No. 1, pp. 125-144, Jul. 1984.
Schmid et al., "Mechanical and electronic manipulation of nanometer-sized wires," Nanotechnology, vol. 5, pp. 26-32, 1994.
Fink et al., "Coherent point source electron beams," Journal of Vacuum Science & Technology B: Microelectonics and Nanometer Structures, Nov. 1990, vol. 8, Issue 6, pp. 1323-1324.
Purcell et al., "Characterization of atomic-size metal ion sources," Journal of Vacuum Science & Technology B: Microelectronics and Nanometer Structures, Jan. 2001, vol. 19, Issue 1, pp. 79-86.
Thompson et al., "Towards a commercial gas field ion source," Proceedings of SPIE, vol. 2437.
Wilbertz et al., "Recent Progress in gas field ion source technology," Proceeding of SPIE, vol. 2194.
Mutsaers, "Nuclear Microprobe Design," Nuclear Instruments & Methods in Physics Research, Section—B: Beam Interactions with Materials and Atoms, Elsevier, Amsterdam, NL, vol. 113, No. 1, Jun. 1996, pp. 323-329.
Jaksic et al., "New Developments in IBIC for the Study of Change Transport Properties of Radiation Detector Materials," Nuclear Intruments & Methods in Physics Research, Section—B: Beam Interactions with Materials and Atoms, Elsevier, Amsterdam, NL, vol. 158, No. 1-4, Sep. 2, 1999, pp. 458-463.
Butz et al., "From Micro- to Nanoprobes: Auspices and Horizons," Nuclear Intruments & Methods in Physics Research, Section—B: Beam Interactions with Materials and Atoms, Elsevier, Amsterdam, NL, vol. 113, No. 1, Jun. 1996, pp. 317-322.
Tondare V. N., "Quest for high brightness, monochromatic noble gas ion sources," J.Vac.Sci.Technol., A 23, 1498 (2005).
Grivet et al., "Ion Microscopy: History and Actual Trends," Ann NY Acad Sci, 1978 NY Acad of Sci, vol. 306, Feb. 23, 1977, pp. 158-182.
Magnan, "The Proton Microscope," Nucleonics, vol. 4, No. 4, Apr. 1949, pp. 52-66.

Chanson et al., "Sur les premieres images obtenues avec un microscope protonique," Comptes Rendus Hebdomadaires des Seances de l'Academie des Sciences France, vol. 233, Dec. 3, 1951, pp. 1436-1438.

Knoll et al., "Das Elektronenmikroskop" Zeitshrift fur Physik Germany, vol. 78, No. 5-6, Oct. 4, 1932, pp. 318-339.

Breese et al., "Ion optical study of a transmission ion microscope," Muclear instruments & Methods in Physics Research, Section—B: Beam Interactions with Materials and Atoms, Elsevier, Amsterdam, NL, vol. 158, No. 1-4, Sep. 2, 1999, pp. 236-240.

Valdiviez et al., "The mechanical design of a proton microscope for radiography at 800 MeV,"Institute of Electrical and Electronics Engineers: Proceedings of the 2003 Particle Accelerator Conference. PAC 2003. Portland, OR, May 12-16, 2003, Particle Accelerator Conference, New York, NY: IEEE, US. vol. 1 of 5, May 12, 2003.

Levi-Setti et al., "High Resolution Scanning Ion Probes," Applications to Physica and Biology, Nuclear Instruments & Methods, vol. 168, pp. 139-149, 1980.

Levi-Setti, "Proton Scanning Microscopy: Feasiblity and Promise," Scanning Electron Microscopy. Proceedings of The Annual Scanning Electron Microscope Symposium, Chicago, IL., pp. 125-134, Apr. 11, 1974.

Levi-Setti et al., High Resolution Scanning Ion Probes: Application to Physics and Biology, Nuclear Instruments & Methods, vol. 168, pp. 139-149, 1980.

* cited by examiner

SCANNING TRANSMISSION ION MICROSCOPE

BACKGROUND OF THE INVENTION

This invention relates to ion microscopy and more particularly to a scanning transmission ion microscope.

The structure of thin samples can currently be analyzed by scanning transmission electron microscopes (STEM) or by transmission electron microscopes (TEM). Both of these instruments detect changes in the primary electron beam when it interacts with the electronic structure of a sample. The focused probe used in STEM will, upon exit from the sample, provide information about the atomic spacing in the material and the atomic species through interactions that are sensitive to the atomic number Z at the beam position. TEM illuminates the sample all at once with a uniform electron beam so that the structure of the sample being examined imparts spatial information onto the beam. By looking at either the bright field (electrons which are transmitted) or dark field (electrons that are scattered), different types of sample information can be extracted. A TEM is a large, complex, expensive tool utilizing very high energy electrons. The use of very high energy electrons is an operational burden. STEM is somewhat simpler but cannot yield the same resolution as TEM. Its main advantage is greater contrast dependence on Z, allowing species characterization.

Atomic level surface structure from thick samples is obtainable by scanning tunneling microscopy (STM) and, to a lesser extent, by atomic force microscopy (AFM). These are slow methods that require mechanically scanning a very fine needle-shaped tip over the sample. These methods cannot provide information on what is below the top atomic layer of the sample, however.

A detailed understanding of the operation of the above-mentioned, presently available microscopes is held by many persons skilled in the art of high resolution microscopes. Detailed information on the theory of operation and the applications of these microscopes is readily available in the public domain. Commonly available publications include, but are not limited to, classroom text books, scientific publications, microscope vendor publications as well as various documents commonly available in libraries such as the United States Library of Congress. There are also many patents that cover these commonly available microscopes. An example of a commonly available publication provided by a microscope vendor is JEOL News, Volume 37E, Number 1, 2002. Textbooks that teach the above described microscopes include the following:

1. *Scanning Electron Microscopy and X-Ray Microanalysis* by Joseph Goldstein (Editor)

2. *Scanning and Transmission Electron Microscopy: An Introduction* by Stanley L. Flegler, et al.

3. *High Resolution Focused Ion Beams: FIB and Its Applications* by Jon Orloff

4. *Materials Analysis Using a Nuclear Microprobe* by Mark B. H. Breese

5. *Scanning Probe Microscopy and Spectroscopy: Theory, Techniques, and Applications* by Dawn Bonnell (Editor)

SUMMARY OF THE INVENTION

In one aspect, the scanning transmission ion microscope of the invention includes a bright helium ion source to generate an ion beam and a focusing electrostatic optical column to focus the ion beam. A translation stage supports a sample to receive the focused ion beam. A detector responds to ions transmitted through the sample to generate a signal from which properties of the sample may be displayed. In a preferred embodiment, a cold finger is provided to vary temperature of the sample. It is also preferred that the whole microscope system be enclosed within a vacuum environment. It is also preferred that a computer control a precise placement of the ion beam on the sample. An electron beam may be provided to neutralize charge on an insulating sample. Suitable ion beam energy is in the range of 1,000 V to 1,000 keV.

DETAILED DESCRIPTION OF THE PREFERRED EMBODIMENTS

Figure 1:
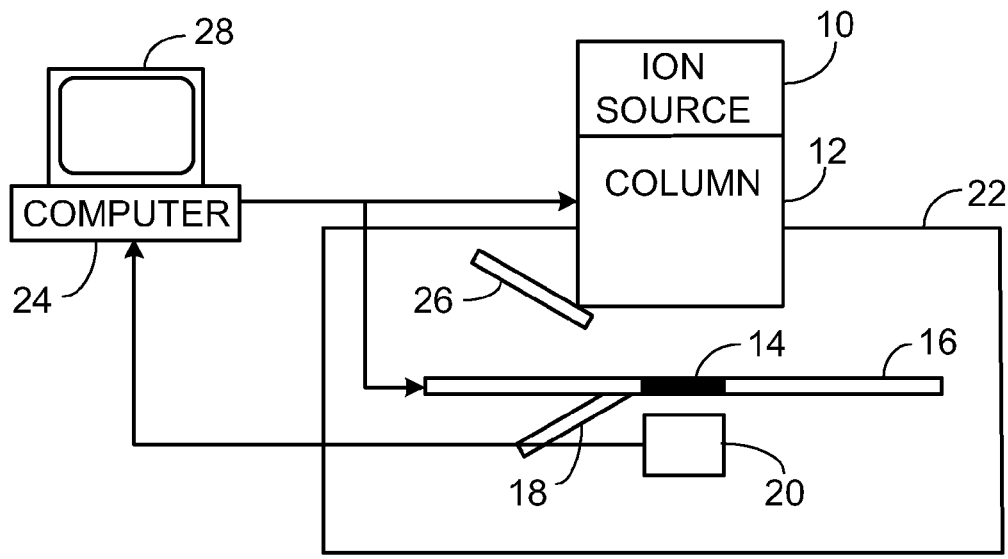
FIG. 1 is a schematic illustration of one embodiment of the microscope of the invention.

With reference first to FIG. 1, an ultra bright helium ion source 10 sends a beam of helium ions down focusing electrostatic column 12. The ions impinge upon a sample 14. The sample 14 is mounted on a translation stage 16. The sample holder 16 may be equipped with a cold finger 18 to allow variation of sample 14 temperature.

Ions transmitted through the sample 14 are detected by a detector 20. A vacuum enclosure 22 surrounds the sample 14 and the detector 20 as shown. A computer 24 provides fine placement of the ion beam on the sample 14 by providing deflection voltages that may or may not be amplified along with optical control voltages that are amplified by high voltage supplies (not shown) allowing control of beam focus and deflection. A low energy charge neutralizing electron beam unit 26 provides the ability to keep charge from building up on an electrically insulating sample.

With the ion beam focused to sub-nanometer size, it is rastered over the sample that has been preprocessed to sub-micron thickness.

The high brightness ion source 10 produces a helium ion beam with energy in the range of 1,000 V to 1,000 keV. A suitable bright ion source is described in "Ion Sources for Nanofabrication and High Resolution Lithography", J. Melngailis, IEEE Proceedings of the 2001 Particle Accelerator Conference, Chicago, Ill. (2002), the contents of which are incorporated herein by reference. See, also "Growth and Current Charities of a Stable Field Ion Emitter," K. Jousten et al., Ultramicroscope 26, pp. 301-312 (1988) and "Maskless, Resistless Ion Beam Lithography Process," Qing Ji, Ph.D. Dissertation, Department of Electrical Engineering and Computer Sciences, University of California, Berkeley (2003), the contents of both of which are incorporated herein by reference. By limiting the number of emission sites where the gas is shared, a notable increase in current and current density from the remaining emitting sites occurs. Because of its long range in materials, the helium ion beam would traverse the entire sample 14 and exit from the back with great efficiency. The ion current registered in the detector 20 is read by the control computer 24. Thus, information on the ion signal as a function of deflected position of the beam can be gathered at the control computer 24 and displayed on an output screen 28 showing an image that reflects properties of the sample 14.

Figure 2:
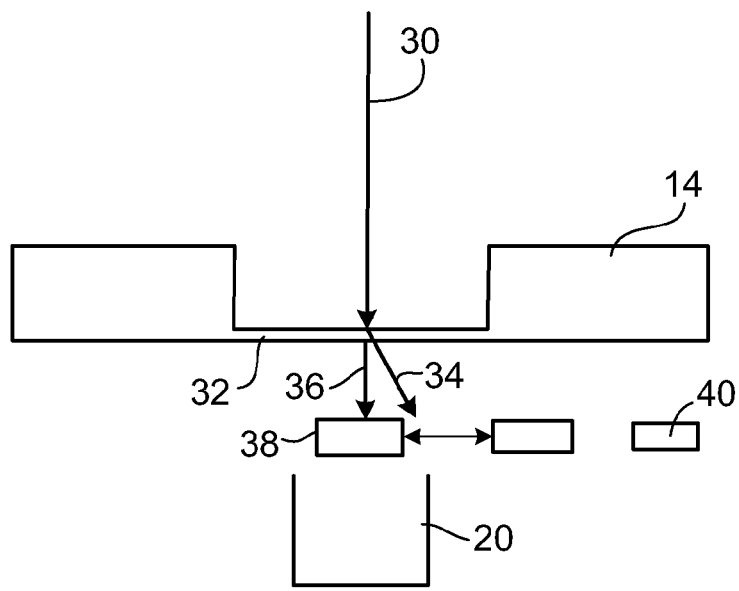
FIG. 2 is a schematic illustration showing the sample end detector regions more clearly.

The detector portion of this embodiment of the invention is shown in FIG. 2 in more detail. The focused ion beam 30 impinges on the sample 14 that has been thinned in a predesignated area 32. Upon collisions with the lattice atoms of the sample 14, the helium ions undergo either large or small angle scattering. The former will constitute a dark field signal 34 while the latter will constitute a bright field signal 36. A pair of interchangeable apertures 38 and 40 are provided to select either the dark or bright field signal, respectively. The chosen component of the signal is collected in the ion detector 20 for recording in the control computer 24.

An alternate system is contemplated without the use of the computer beam control system. Two analog ramp generators, with one at a significantly higher frequency than the other, can both scan the helium ion beam and an analog driven CRT at the same time. The brightness of the CRT beam will be modulated by a signal from the transmission detector providing the equivalent of a gray scale (black and white) picture.

Yet another system can use a combination of computer control and ramp generators. In such a system, the computer detects the voltages of the ramp generators and creates a coherent picture by measuring these ramp generators and the output of the transmission detector.

The control of optical elements may be accomplished by manual means such as a knob or slider which, in turn, provides signals to certain high voltage supplies.

The scanning transmission ion microscope of the invention takes advantage of the unusually long range of helium ions in matter. The range can be 200 times longer than for a heavy ion such as gallium. Because the ion source used with the microscope disclosed herein can achieve sub-nanometer beam diameter, the microscope of the invention can achieve that which was previously possible only with an electron beam.

The collection of the transmitted (bright field) and/or scattered (dark field) ions will provide structural information about the sample in a manner never achieved before. Further, the interaction dynamics of an ion beam with a sample material is different from interactions with an electron beam. There will be more effects from atomic centers and fewer effects from the electronic structure of the sample. This may best be explained as nuclear contrast. In a bright field picture, dark pixels are the result of ions that interact with the atomic nuclei in the sample that are then scattered away from the detector or absorbed in the sample. Bright pixels in the image are the result of ions that are not scattered or absorbed by the atoms in the sample. In the case of a dark field picture, the contrast is reversed, or inverted, from the previous situation.

The system disclosed herein will likely be simpler, smaller, and weigh less than a STEM or TEM because of the electrostatic optics. The contrast in the displayed image will also be greater than for a STEM or TEM. The picture will have more elemental contrast and may be enhanced with a charge neutralizer.

The temperature of the sample may change the quality of the resulting image. The ion beam may cause atoms in the sample to vibrate thereby providing yet another contrast mechanism. Because crystal orientation may be important, a tilting sample holder is preferred and the sample holder should also provide an x-y motion. Picture contrast may also be affected by voltage and the comparison of pictures taken at different voltages can provide yet another contrast mechanism.

The energy loss of the ion beam at each position also carries information about the composition of the sample material. While a traditional STIM uses high energy (MEV) ion beams produced in accelerators, their resolution is nonetheless limited to 50-100 nm. Those of ordinary skill in the art will appreciate that low energy ion scatter spectroscopy may be utilized to identify the elements in the sample.

It is recognized that modifications and variations of the invention disclosed herein will be apparent to those of skill in the art and it is intended that all such modifications and variations be included within the scope of the appended claims.

What is claimed is:

1. Scanning transmission ion microscope comprising:
   a bright helium ion source to generate an ion beam;
   a focusing electrostatic optical column to focus the ion beam;
   a translation stage supporting a sample to receive the focused ion beam; and
   a detector responsive to ions transmitted through the sample.

2. The microscope of claim 1 further including a cold finger to vary sample temperature.

3. The microscope of claim 1 further including structure to maintain the microscope in a vacuum environment.

4. The microscope of claim 1 further including computer controlled placement of the ion beam on the sample.

5. The microscope of claim 1 further including a charge neutralizing electron beam to neutralize charge on an insulating sample.

6. The microscope of claim 1 wherein the ion beam energy is in the range of 1,000 V to 1,000 keV.

7. A scanning transmission ion microscope, comprising:
   an ion source capable of generating a helium ion beam;
   a translation stage capable of supporting a sample;
   a column capable of directing the ion beam from the ion source to the sample; and
   a detector capable of detecting ions transmitted through the sample.

8. The scanning transmission ion microscope of claim 7, wherein the ion source is capable of generating a helium ion beam.

9. The scanning transmission ion microscope of claim 7, wherein the ion source is capable of generating a helium ion beam having an energy in the range of 1,000 V to 1,000 KeV.

10. The scanning transmission ion microscope of claim 7, further comprising a computer configured to control placement of the ion beam on the sample.

11. The scanning transmission ion microscope of claim 10, wherein the computer provides optical control voltages and deflection voltages to the column.

12. The scanning transmission ion microscope of claim 7, further comprising an electron beam unit capable of producing an electron beam that can be directed to the sample.

13. The scanning transmission ion microscope of claim 7, further comprising a cold finger configured to allow variation of a temperature of the sample.

14. The scanning transmission ion microscope of claim 7, further comprising apertures between the translation stage and the detector so that the apertures select ions that pass from the sample to the detector.

15. The scanning transmission ion microscope of claim 7, further comprising a computer configured to display a signal generated by the detector.

16. The scanning transmission ion microscope of claim 15, wherein the computer is configured to control placement of the ion beam on the sample.

17. The scanning transmission ion microscope of claim 7, further comprising analog ramp generators configured to scan the ion beam.

18. The scanning transmission ion microscope of claim 7, wherein the column comprises optical elements, and the scanning transmission ion microscope further comprises a device configured to manually control the optical elements.

19. A method, comprising:
   determining structural information about a sample based on ions in a helium ion beam that pass through the sample, the ion beam being generated using an ion beam source.

20. The method of claim 19, wherein the ion beam is a helium ion beam.

* * * * *

UNITED STATES PATENT AND TRADEMARK OFFICE
CERTIFICATE OF CORRECTION

PATENT NO.      : 7,321,118 B2
APPLICATION NO. : 11/147102
DATED           : January 22, 2008
INVENTOR(S)     : Billy W. Ward It is certified that error appears in the above-identified patent and that said Letters Patent is hereby corrected as shown below:

On Title page 3, in field 56, in column 2, under "Other Publications", line 4, delete "Physica", insert --Physics--.

Signed and Sealed this

Ninth Day of December, 2008

JON W. DUDAS
*Director of the United States Patent and Trademark Office*